United States Patent
Lizardi

[11] Patent Number: 5,944,724
[45] Date of Patent: Aug. 31, 1999

[54] SUTURE ANCHOR INSERTION SYSTEM

[75] Inventor: José E. Lizardi, Franklin, Mass.

[73] Assignee: Mitek Surgical Products, Inc., Westwood, Mass.

[21] Appl. No.: 08/961,290

[22] Filed: Oct. 30, 1997

[51] Int. Cl.[6] .................................................. A61B 17/04
[52] U.S. Cl. ......................................... 606/104; 606/232
[58] Field of Search ................................... 606/104, 232, 606/139

[56] References Cited

U.S. PATENT DOCUMENTS

| | | | |
|---|---|---|---|
| 4,712,542 | 12/1987 | Daniel et al. | 128/92 V |
| 4,946,468 | 8/1990 | Li | 606/232 |
| 5,002,550 | 3/1991 | Li | 606/139 |
| 5,021,059 | 6/1991 | Kensey et al. | 606/213 |
| 5,037,426 | 8/1991 | Goble et al. | 606/96 |
| 5,071,420 | 12/1991 | Paulos et al. | 606/99 |
| 5,078,730 | 1/1992 | Li et al. | 606/228 |
| 5,100,417 | 3/1992 | Cerier et al. | 606/139 |
| 5,578,057 | 11/1996 | Wenstrom, Jr. | 606/232 |
| 5,584,860 | 12/1996 | Goble et al. | 606/232 |
| 5,814,051 | 9/1998 | Wenstrom, Jr. | 606/104 |

FOREIGN PATENT DOCUMENTS

WO9400079  6/1994  WIPO ............................. A61F 2/08

*Primary Examiner*—Gary Jackson
*Attorney, Agent, or Firm*—Nutter, McClennen & Fish, LLP

[57] ABSTRACT

A system for inserting suture anchors includes a suture anchor insertion tool, a suture anchor, a length of suture thread and any needles pre-attached thereto. The suture anchor insertion tool having a handle, an elongate suture anchor inserting member, a suture thread retaining cap provided on the handle, an internal retaining cavity formed integrally with the handle and a cover member that is selectively positionable so as to enclose the internal cavity.

28 Claims, 12 Drawing Sheets

SUTURE ANCHOR INSERTION SYSTEM

CROSS-REFERENCE TO RELATED APPLICATIONS

Not Applicable.

STATEMENT REGARDING FEDERALLY SPONSORED RESEARCH

Not Applicable.

FIELD OF THE INVENTION

The invention relates to surgical systems for inserting a suture anchor into bodily tissue. More particularly, the invention relates to a suture anchor insertion tool which may be used to insert a suture anchor having a length of suture thread attached thereto.

BACKGROUND OF THE INVENTION

Systems and devices for anchoring sutures to bone are commonly used in medical or surgical operations. Anchored sutures are typically used to attach soft tissue, such as ligaments, tendons and muscles, to bone or inanimate objects, such as prostheses. The attachment may hold the tissue to a bone for an extended period of time to allow healing to occur. Alternatively, the attachment may be used to hold tissue in place temporarily during a surgical procedure to help perform or optimize that procedure.

Suture anchors typically have an anchor body, a suture attachment feature and a bone engaging feature for retaining the suture anchor within bone. The suture anchor may be inserted into a preformed hole in the bone, or with threaded (i.e., screw-type) suture anchors, the suture anchor may be screwed into the bone, with or without a preformed bore, in the manner of a common screw. Examples of suture anchors and suture anchor installation tools may be found in U.S. Pat. Nos. 4,946,468; 4,968,315; 5,002,550; 5,207,679; 5,217,486; 5,411,506; 5,411,523; 5,520,696; 5,522,845; 5,578,057 and 5,584,860.

Small suture anchors can be difficult to handle and manipulate with some existing suture anchor insertion tools. In particular, it can be difficult to retain a small suture anchor on the insertion tool until such time as the anchor is inserted into bone. Because of their small size, these suture anchors are difficult to reattach to the insertion tool in a surgical environment if they become prematurely separated from the insertion tool.

Suture management during and after insertion of the anchor can be challenging as well. Smaller suture anchors, which are often pre-loaded onto the insertion tool and pre-threaded with suture thread, must be managed to ensure that the anchors and any attached suture thread and needles are properly delivered to the surgical site.

One known approach to suture management is to carry the suture thread inside a cannulated suture anchor insertion tool, such as disclosed in U.S. Pat. Nos. 5,584,860, 5,411, 506 and 5,258,016. This approach is sometimes used with threaded suture anchors so that the suture thread may be managed even while twisting the insertion tool to insert the threaded anchor. In some instances, and particularly with smaller suture anchors, the suture anchor mating area on the distal portion of the insertion tool is so small that it is difficult to pass suture needles therethrough. Thus, if needles are required for post-anchor installation suturing procedures, it can be difficult to deliver the needles to the surgical site with the insertion tool.

Other suture anchor insertion tools, such as the suture anchor insertion tool of U.S. Pat. No. 5,002,550, provide arcuate groove storage areas on the body of the tool where needles may be stored. A surgeon uses a tool, such as needle-nosed forceps, to remove the needles from the grooves.

Still other suture anchor insertion tools manage suture thread attached to the anchor by equipping the installation tool with external posts or surfaces, about which the suture thread is wound. The winding and unwinding of suture thread can also present surgical challenges when suture needles are pre-attached to the thread.

Perhaps as a result of the difficulties in managing suture thread, especially where needles are pre-attached to the thread, some existing suture insertion tools tend to be short, with the suture anchor being maintained very close to the handle portion of the tool. This can cause difficulties in minimally invasive surgical procedures where surgical tools are employed through small incisions in the patient's body, especially where such small incisions are not necessarily in immediate proximity to the preferred suture anchor insertion site.

There is thus a need for a suture anchor insertion tool that can deliver a small suture anchor to a bone attachment site through a small incision in the patient's body while maintaining the suture anchor on the tip of the tool and managing the suture thread and needles at the surgical site without the aforementioned drawbacks. The tool should be long enough to reach desired operative locations under minimally invasive, closed surgical conditions, should provide an efficient means to manage and tension the suture thread and should allow for easy management and delivery of suture needles to the desired site. In addition, the tool should be capable of delivering suture anchors and needles of a variety of sizes to the surgical site.

SUMMARY OF THE INVENTION

The present invention provides a system for inserting suture anchors and a managing any attached lengths of suture thread. The system includes a suture anchor insertion tool having a handle, an elongate suture anchor inserting member, a suture thread retaining member provided on the handle, an internal cavity formed in the handle and a cover member that is selectively positionable so as to expose or enclose the internal cavity.

The system may also include a suture anchor releasably mated to a distal end of the suture anchor inserting member. The suture anchor preferably has attached thereto an intermediate portion of a length of suture thread. Two free ends of the suture thread, and any needles attached thereto, extend from the suture anchor. The free ends of the suture thread and any attached needles may be stored within the internal cavity of the insertion tool. The suture thread may be maintained in a state of tension on the tool by pulling the thread to create the tension, then actuating the suture thread retaining member so as to capture and retain the suture thread in a state of tension.

The suture thread retaining member may include a base member and a cap member. The base member, which is disposed on the handle, is generally cylindrical and has a peripheral rim. The suture thread retaining member has a first, open position, wherein the cap member is spaced apart from the peripheral rim of the base member and a second, closed position, wherein the cap member mates with the base member in proximity to the peripheral rim. Preferably, at least one of the cap member and the base member are resilient so that a suture thread placed across the peripheral rim may be captured in a state of tension by the mating of the cap member and the base member. The suture thread retaining member is preferably disposed within the internal cavity of the handle.

In one embodiment, the internal cavity has proximal and distal portions. The suture thread retaining cap may be located in the distal portion of the internal cavity and the suture thread and any needles attached thereto may be stored in the proximal portion of the cavity. The cover member may comprise a sliding door matable with a side wall of the handle having three positions: a first, open position wherein the cavity is uncovered so as to allow access to both the proximal and distal portions of the cavity; a second, closed position wherein the door covers the proximal and distal portions of the cavity; and a third, intermediate position wherein the door covers the proximal portion of the cavity in a manner sufficient to retain at least one suture needle and thread within the cavity, but does not cover the distal portion.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
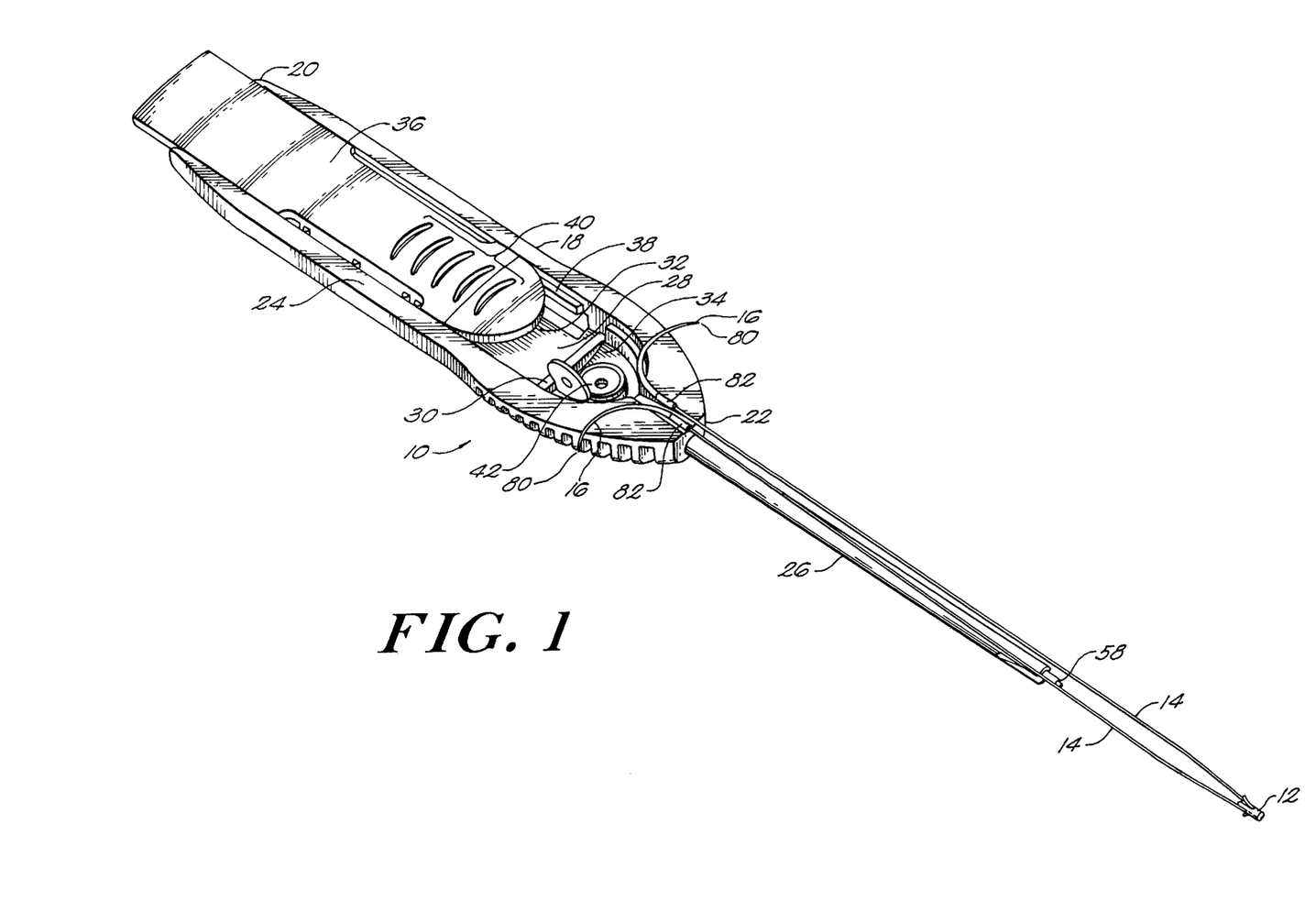
FIG. 1 is a perspective view of a suture anchor insertion system of the invention.

A suture anchor insertion system of the invention, illustrated in FIG. 1, has a suture anchor insertion tool 10, a suture anchor 12, a length of suture thread 14 and at least one suture needle 16. The suture anchor insertion tool 10, illustrated in FIGS. 1 to 3, includes a handle portion 18 having proximal and distal ends 20, 22 and a side wall 24 disposed between the ends 20, 22, and an elongate suture anchor insertion member 26 extending from the distal end 22 of the handle 18. The suture anchor insertion tool 10 may be made from a variety of materials known to those of ordinary skill in the art to be useful for constructing surgical tools. In one embodiment, the handle 18 is formed from a polymeric material such as polyethylene or a copolymer thereof and the suture anchor insertion member 26 is formed from a metal such as stainless steel.

The side wall 24 of the handle 18 defines an internal cavity 28 suitable to store the suture thread 14 and any attached suture needles 16. The cavity 28, as best seen in FIG. 1, is divided by separating member 30 into a proximal portion 32 and a distal portion 34. A cover member 36 is slidably disposed on the handle 18, disposed upon the side wall 24, so as to enclose at least a portion of the cavity 28. Rails 38 (one shown) may be provided in the cavity 28 to slidably engage a portion of the cover member 36 to create the sliding attachment and allow the cover member 36 to slide in a proximal-distal direction. The cover member 36 may also be provided with a thumb grip 40 on a superior surface thereof to allow a surgeon to easily slide the cover member 36 while gripping the handle 18. The handle 18 should be of an appropriate size to allow for handling of the tool by a surgeon with one hand. Generally, the handle 18 may be between about 3 to 6 inches in length.

Figure 2:
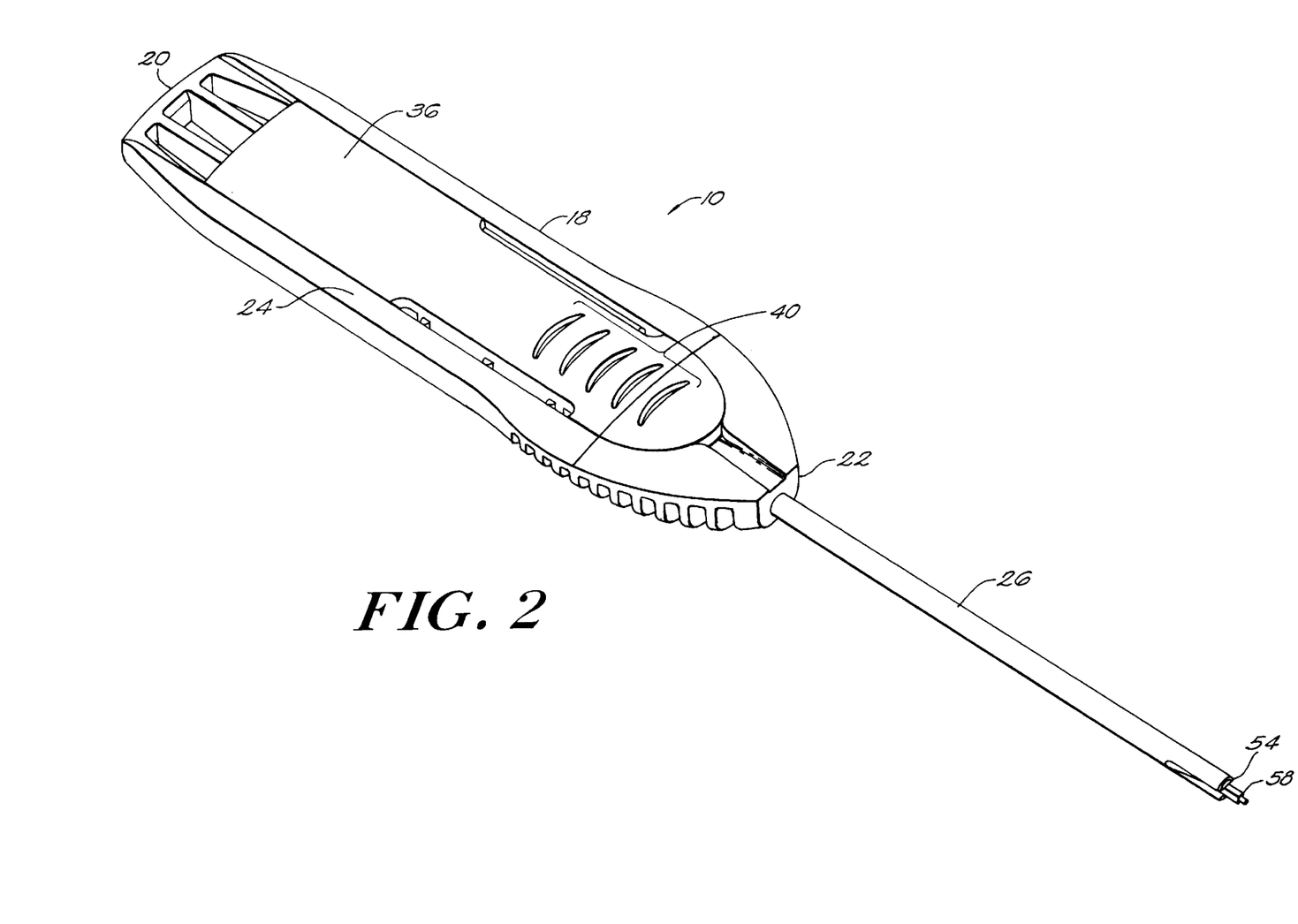
FIG. 2 is a perspective view of a suture anchor insertion tool of FIG. 1 with a cover member shown in a closed position.

As shown in FIG. 1, the cover member 36 is located in its proximal-most position wherein both the proximal and distal portions 32, 34 of the internal cavity 28 are exposed. This proximal-most position is referred to herein as the "open" position of the cover member 36. By contrast, the cover member 36 is illustrated in FIG. 2 in its distal-most or "closed" position wherein the entirety of the internal cavity 28 is closed off and any contents of the cavity 28 are retained therein.

Figure 3:
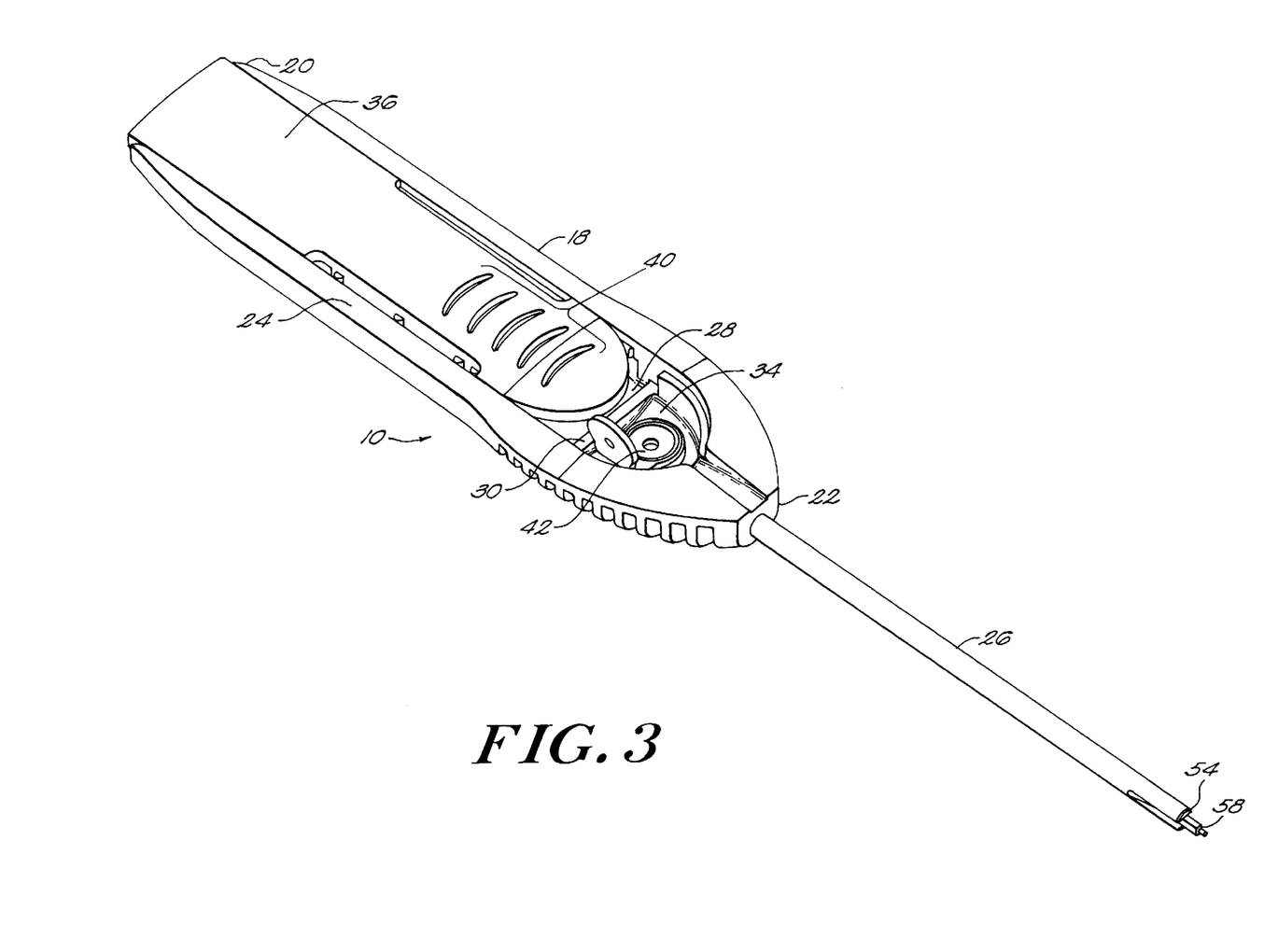
FIG. 3 is a perspective view of a suture anchor insertion tool of FIG. 1 with the cover member shown in an intermediate position.

In addition, the cover member 36 may be placed, as shown in FIG. 3, in an "intermediate" position wherein the proximal portion 32 of the internal cavity 28 is enclosed in a manner sufficient to retain therein at least one suture needle 16 and suture thread 14, but the distal portion 34 of the internal cavity 28 is exposed and accessible. A protuberance (not shown) may be placed on a proximal portion of the handle 18 over which the cover member 36 slides, with a corresponding recess (not shown) provided on an inferior surface of the cover member 36. The protuberance and recess may be located so as to engage when the cover member 36 is placed in the intermediate position, thereby creating a temporary locking condition which retains the cover member 36 in the intermediate position until the cover member 36 is forcibly moved from that position by a user of the tool 10. Of course, a person of ordinary skill in the art may employ a variety of cover member configurations to selectively cover all or portions of the internal cavity 28 to the same effect as the sliding cover member 36 described herein.

The suture anchor insertion tool 10 also includes a suture thread capturing or retaining member 42. Preferably, the suture thread retaining member 42 is provided in the proximal portion 34 of the internal cavity 28. When provided in this location, the suture thread retaining member 42 is accessible to the surgeon when the cover member 36 is selectively moved to its open or intermediate positions, and is enclosed when the cover member 36 is moved to its closed position.

An exemplary suture thread retaining member 42 and its operation are illustrated in FIGS. 4 to 7. The suture thread retaining member 42 includes a cap member 44 and a generally cylindrical base member 46. The base member 46 is fixed to the handle 18 within the proximal portion 34 of the internal cavity 28 and the cap 44 is attached to the base 46 by means of a connecting member 48. The connecting member is preferably resilient so as to allow the cap 44 to be able to move with respect to the base 46. The base member 46 has a peripheral rim 50 which faces out of the internal cavity 28 and generally in a direction towards the cap member 44. Because the exemplary base member 46 is cylindrical, the peripheral rim 50 is round. A person of ordinary skill in the art will readily recognize that other shapes and configuration of the suture retaining member are possible.

Figure 4:
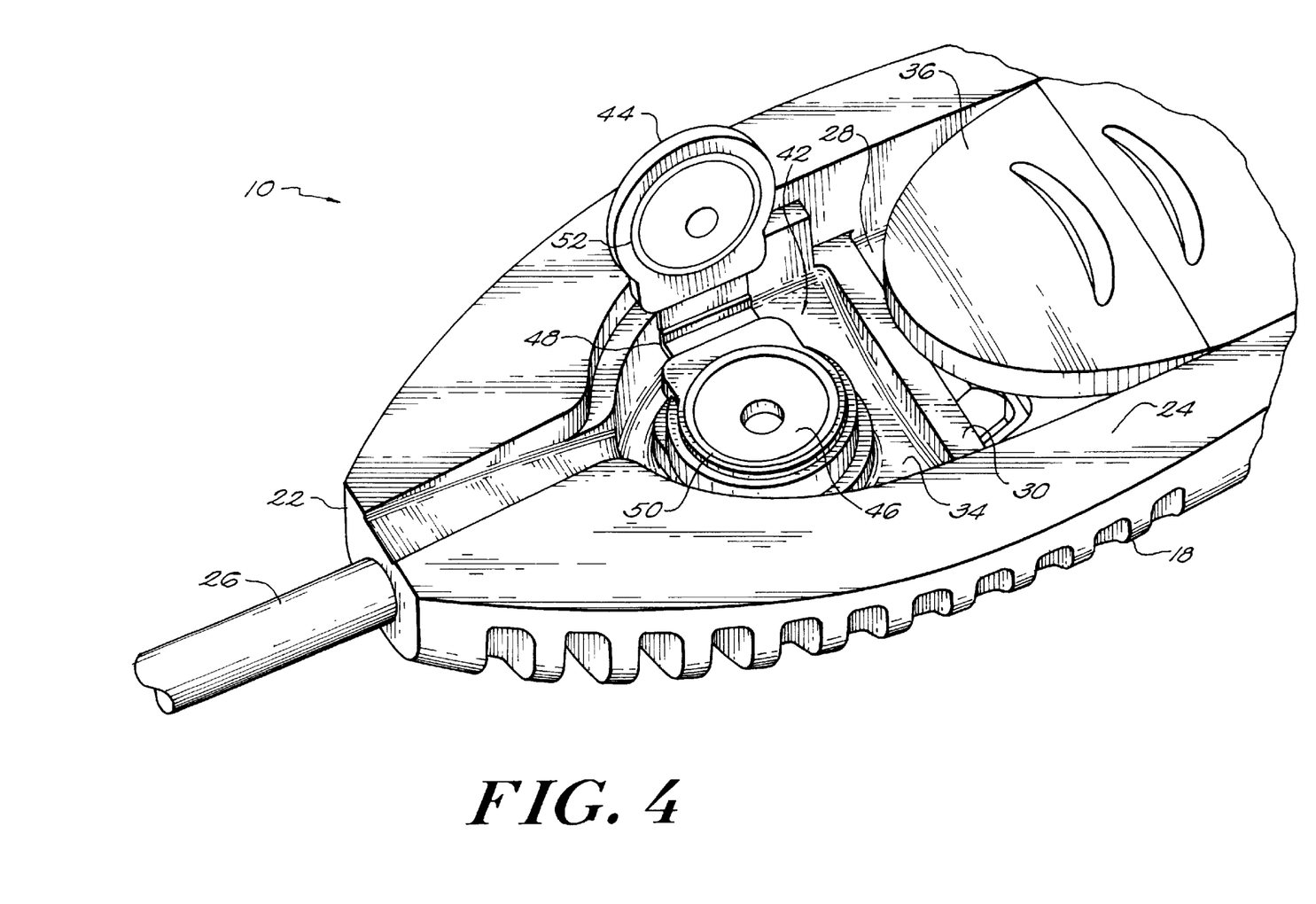
FIG. 4 illustrates a portion of the suture anchor inserting tool of FIG. 1 including a suture retaining member in an open position.
Figure 5:
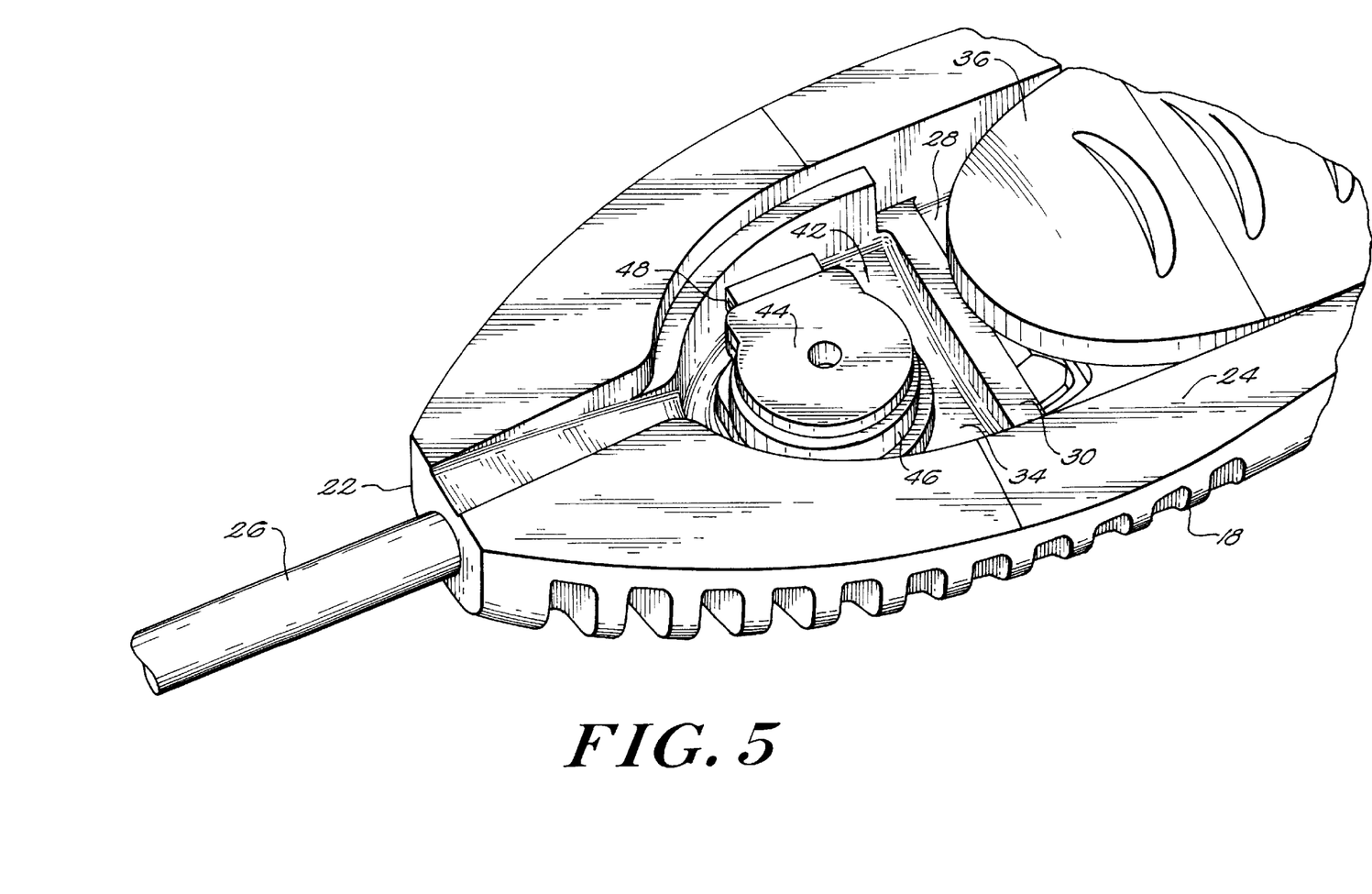
FIG. 5 illustrates the suture retaining member of FIG. 4 in a closed position.

The cap member 44 is generally circular and includes an inferior surface 52 which faces in a direction towards and is matable with the base member 46. The cap 44 may be selectively positioned so that it is spaced apart from the base member 46 as shown in FIG. 4. This position is referred to herein as the "open" position of the suture thread retaining member 42. The inferior surface 52 of the cap member 44 may be angled and dimensioned to form a friction fit around the peripheral rim 50 on the base member 46 when the inferior surface 52 of the cap member 44 is pressed to the peripheral rim 50 of the base member 46. Preferably, at least one of the cap member 44 and the base member 46 is resilient so that a suture thread may be snugly retained between the mated members. This position, shown in FIG. 5, is the "closed" position of the suture retaining member 42.

Figure 6:
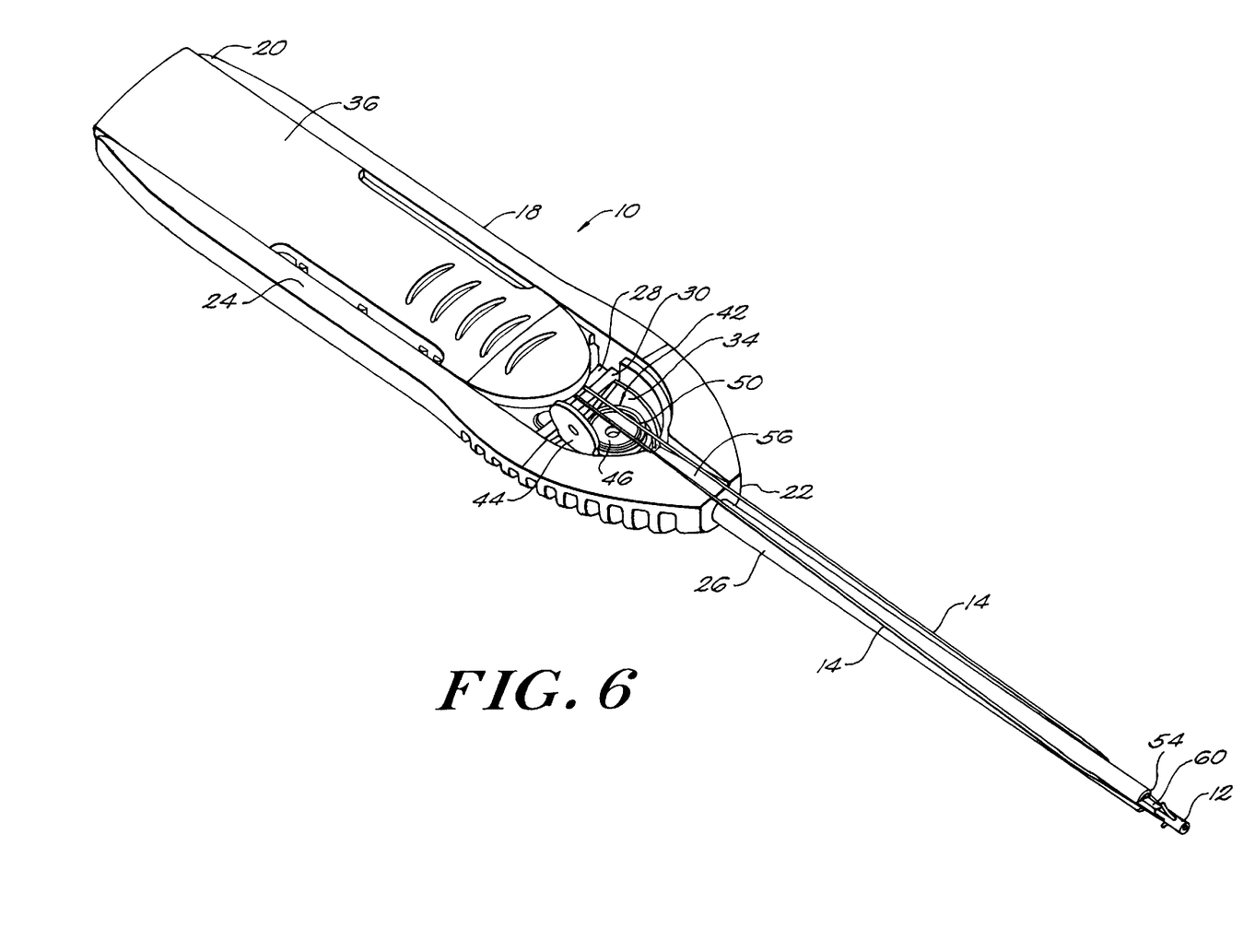
FIG. 6 is a perspective view of the suture anchor insertion system of FIG. 1 with the cover member shown in the intermediate position and the suture retaining member in an open position.
Figure 6A:
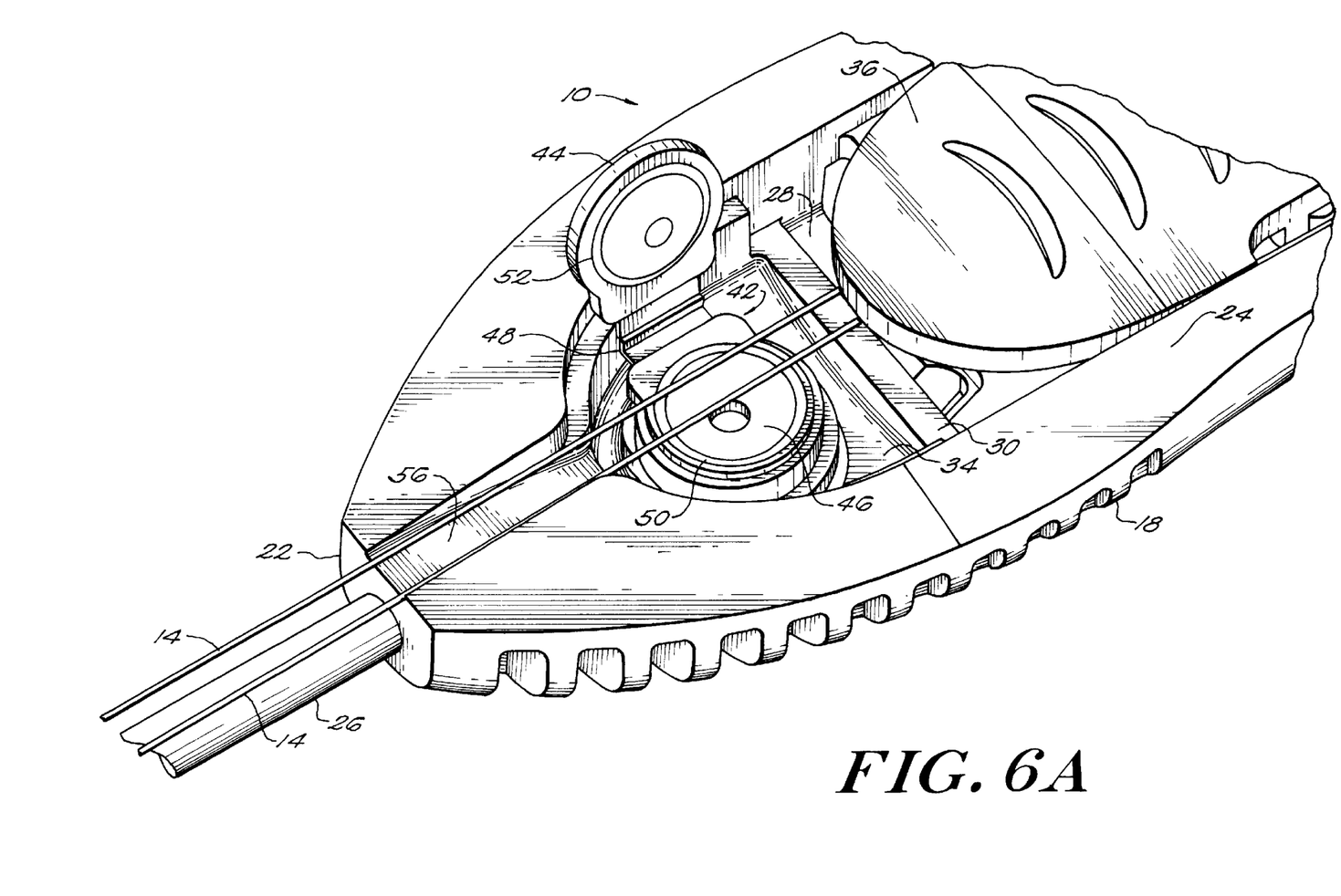
FIG. 6A illustrates a portion of the suture anchor insertion tool of FIG. 6.
Figure 7:
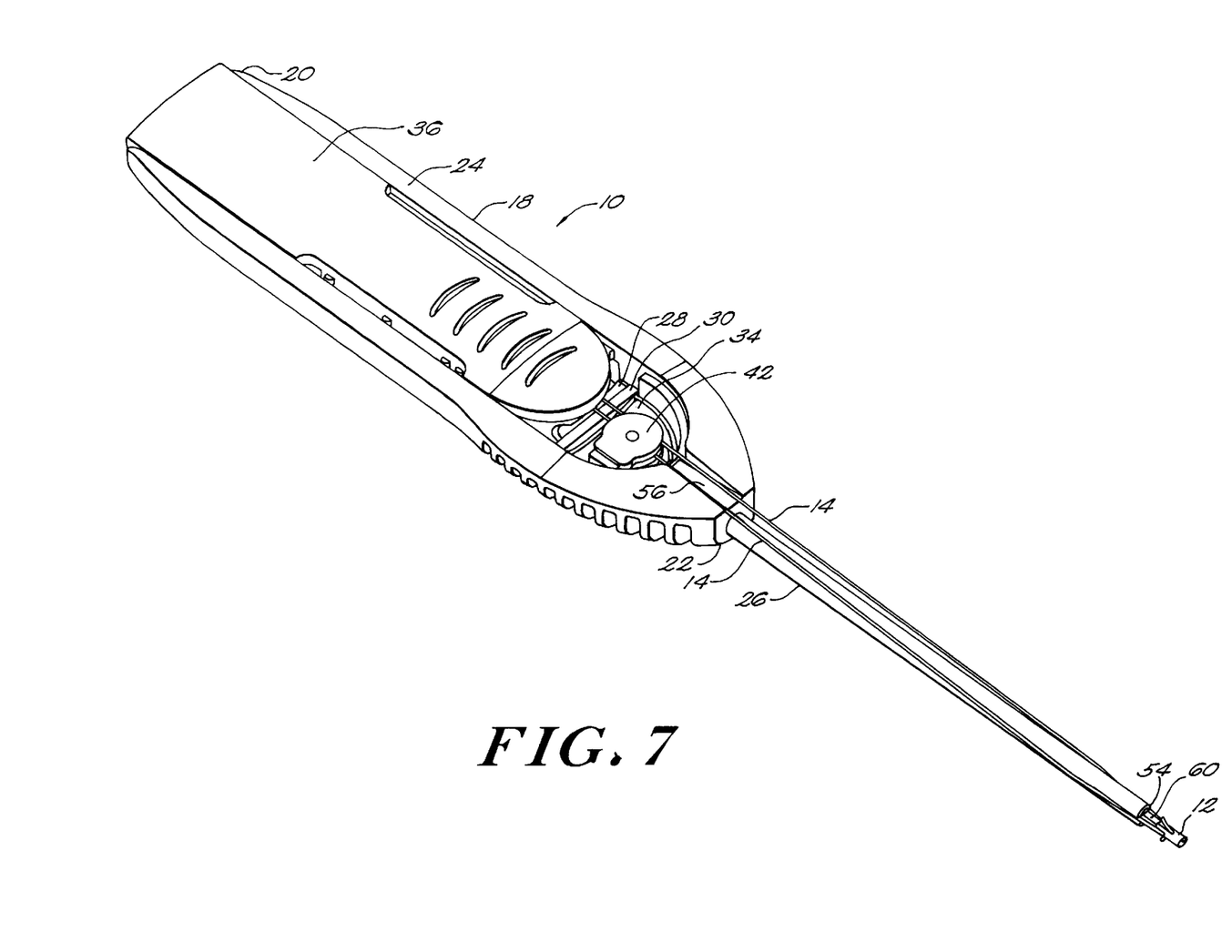
FIG. 7 is a perspective view of the suture anchor insertion system of FIG. 6 with the suture retaining member in a closed position.
Figure 8:
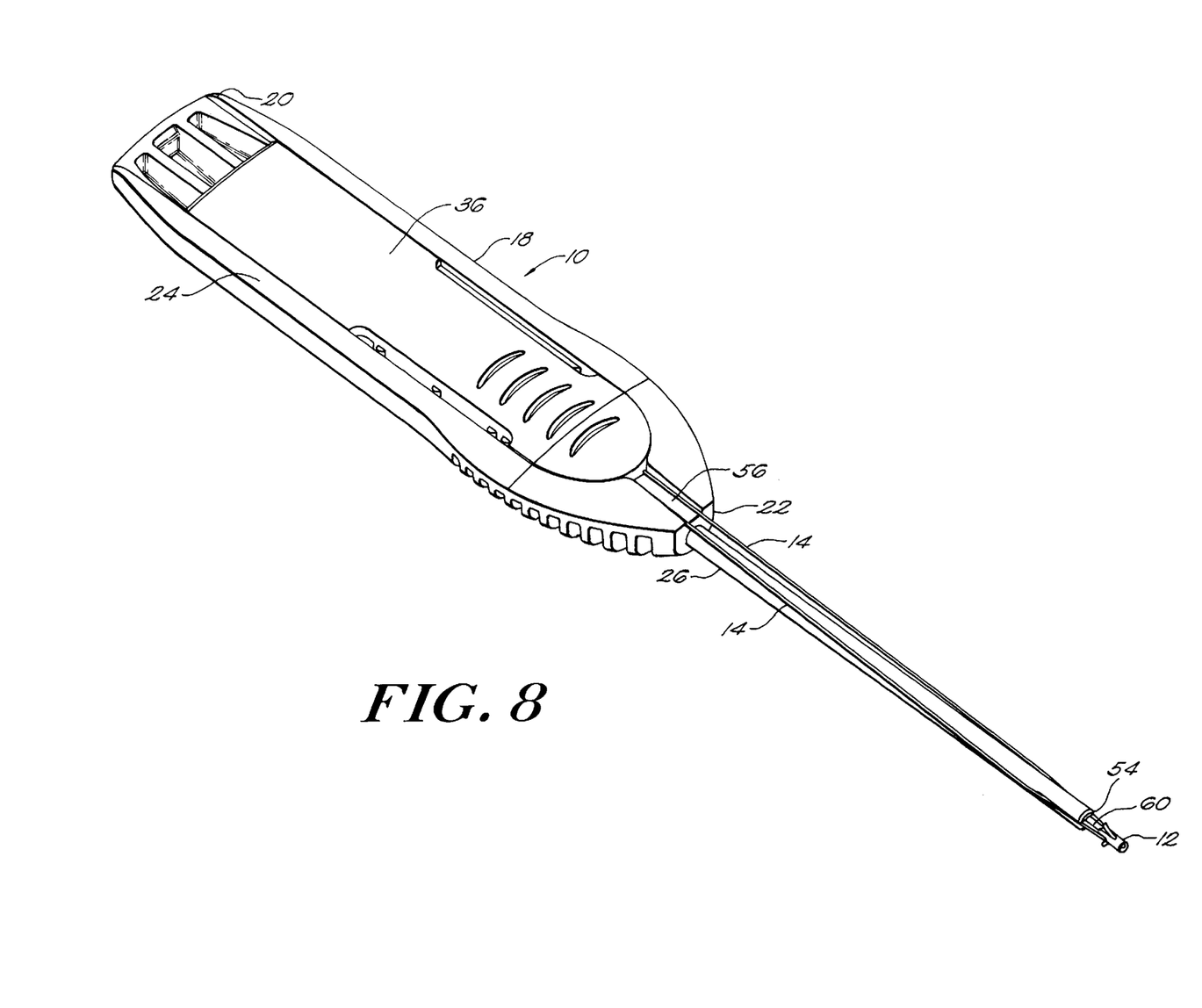
FIG. 8 is a perspective view of the suture anchor insertion system of FIG. 6 with the cover member shown in a closed position.
Figure 9:
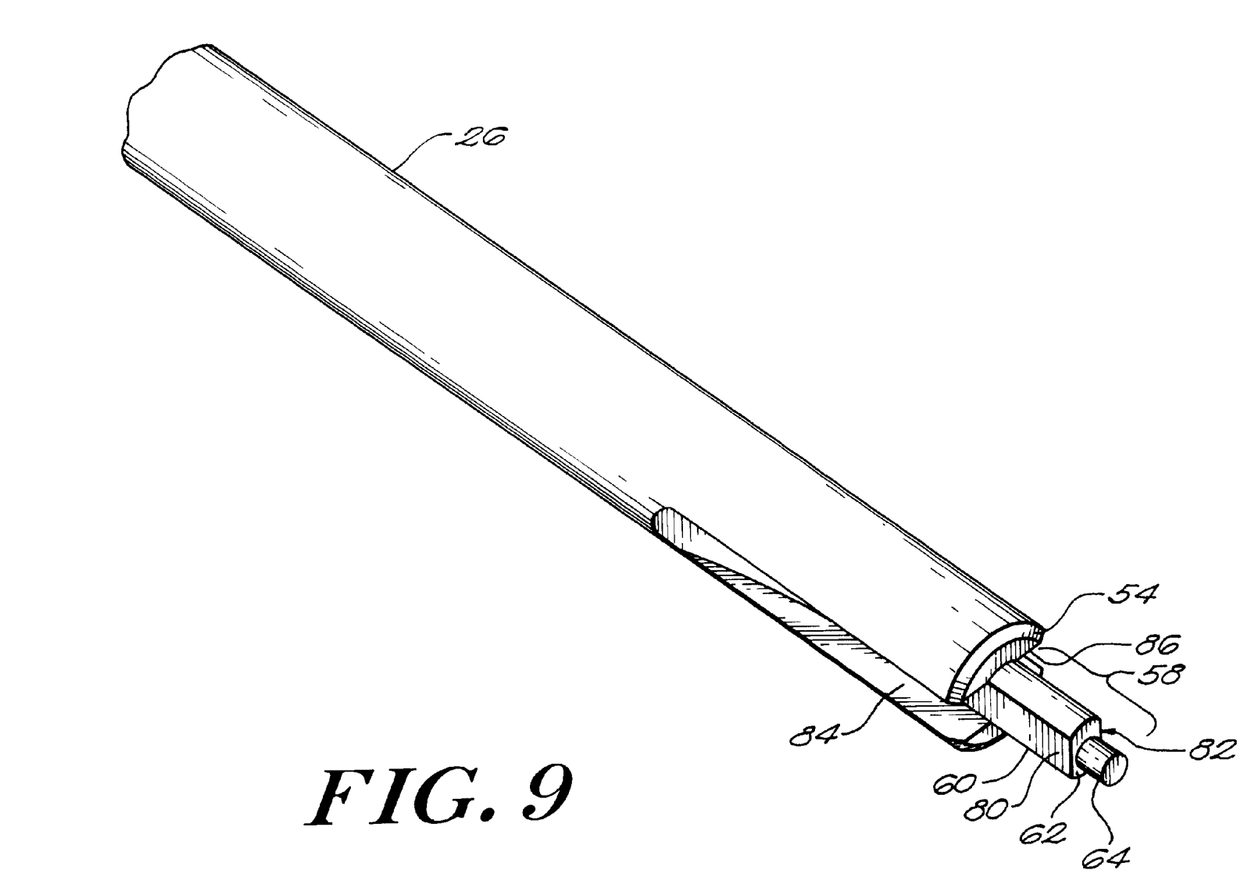
FIG. 9 illustrates the distal end of a suture anchor inserting member of FIG. 1.

The operation of the suture retaining member 42 is illustrated in FIGS. 6 to 8. As shown in FIG. 6, a suture anchor 12 is installed on a distal end 54 of the suture anchor inserting member 26, an intermediate portion of suture thread 14 is retained within the suture anchor 12 and two free ends of the suture thread 14 extend from the suture anchor 12 to the proximal portion 34 of the internal cavity 28 within the handle 18. A groove 56, best seen in FIG. 6A, is provided in the distal end 22 of the handle 18 to direct the suture thread 14 over the base member 46 of the suture retaining member 42 when the suture retaining member 42 is in the open position. The groove 56, extends from the distal end 22 of the handle 18 to the proximal portion 34 of the internal cavity 28 and has a greater depth at the proximal portion 34 of the internal cavity 28 than at the distal end 22 of the handle 18.

The suture retaining member 42 may be placed in a closed position over the suture thread 14 as shown in FIG. 7 by pressing the cap member 44 toward the base member 46 with sufficient force to cause a friction fit between the cap 44 and base 46. When closed, the suture retaining member 42 is capable of retaining the suture thread 14 so that a state of tension is maintained in the suture thread 14 between the suture retaining member 42 and the suture anchor 12 where the position of the suture thread 14 is also restrained. The amount of tension maintained in the suture thread 14 may be varied by opening the suture retaining member 42, pulling the thread 14 to the desired tension, and closing the suture retaining member 42 over the thread 14 to capture the thread 14 and maintain the desired tension.

Next, as shown in FIG. 8, the cover member 36 may be moved to its closed position wherein both the proximal portion 32 of the internal cavity 28, where the suture thread 14 and any attached needles 16 are stored, and the distal portion 34 of the internal cavity, where the suture retaining member 42 is disposed, are enclosed. Enclosing the suture retaining member 42 after the desired tension has been achieved in the suture thread 14 serves to prevent accidental disengagement of the cap member 44 and a consequent loss of tension in the suture thread 14.

As shown in FIGS. 9 to 12, the distal end 54 of the suture anchor insertion member 26 includes a suture anchor seating element 58 having an anchor projecting member 60, an anchor seating face 62 and an anchor seating pin 64. The anchor seating pin 64 should be of small enough cross sectional dimension so as to mate with a seating pin cavity (not shown) provided on the anchor 12 and of sufficient length so as to provide directional stability to a suture anchor 12 engaged with the seating pin 64. The seating pin 64 should also be sufficient, in cooperation with the proximal tension on the suture anchor 12 from the tensioned suture thread 14, to keep the suture anchor 12 properly seated on the suture seating surface 62 during insertion of the tool 10 to the surgical site.

The cross section of the projecting member 60, and hence the anchor seating face 62, should be no larger than the cross section of the suture anchor 12. So dimensioned, the projecting member 60 will fit within a bore in a bone formed to accept the suture anchor 12. Accordingly, a surgeon may, by means of the projecting member 60, seat the suture anchor 12 within a bore below the outer surface of the bone using the suture anchor insertion tool 10. The length of the anchor projecting member 60 may suitably be between about 2 to 8 mm and is more preferably about 5 mm.

Both the suture anchor insertion member 26 and the anchor projecting member 60 may have features suitable for providing clearance for the suture thread 14 as the thread extends proximally from the anchor 12. The otherwise cylindrical anchor projecting member 60 has opposed flat surfaces 80, 82 aligned with the suture thread 14 so as to provide clearance for the suture thread 14 when the anchor projecting member 60 is inserted within a bore in a bone. Similarly, grooves 84, 86 may be formed in the distal portion of the suture anchor insertion member 26 to provide clearance for the suture thread 14 and to prevent the suture thread 14 from being damaged when the tool 10 is inserted within a patient to a surgical site.

The length of the suture anchor insertion member 26 may be selected for specific applications of the tool 10 by a person of ordinary skill in the art. Generally, the suture anchor insertion member 26 should be long enough to extend from a portal formed for the purpose of performing a closed surgery to the surgical site. Under these circumstances, the suture anchor insertion member 26 may generally be between about 2 to 6 inches in length.

Figure 10:
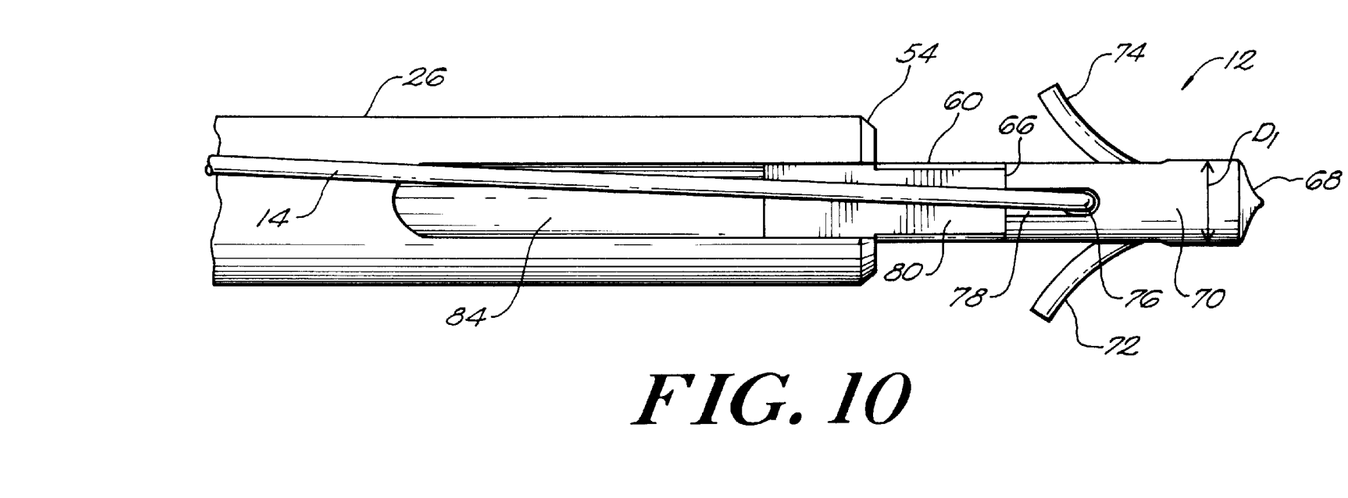
FIG. 10 illustrates the distal end of the suture anchor inserting member of FIG. 9 with a suture anchor seated thereon.
Figure 11:
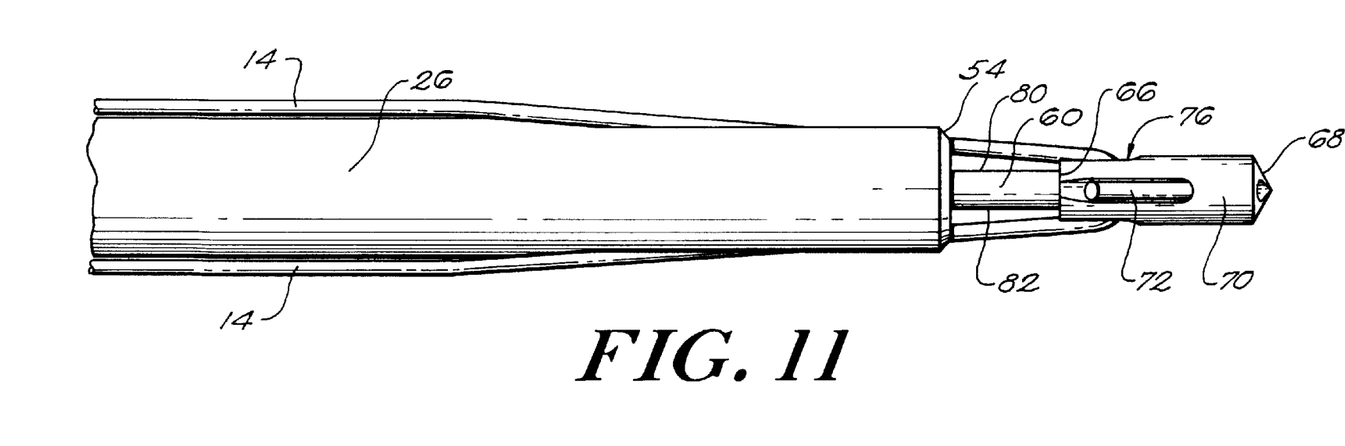
FIG. 11 provides an additional view of the suture anchor inserting member and suture anchor of FIG. 10 rotated 90°.
Figure 12:
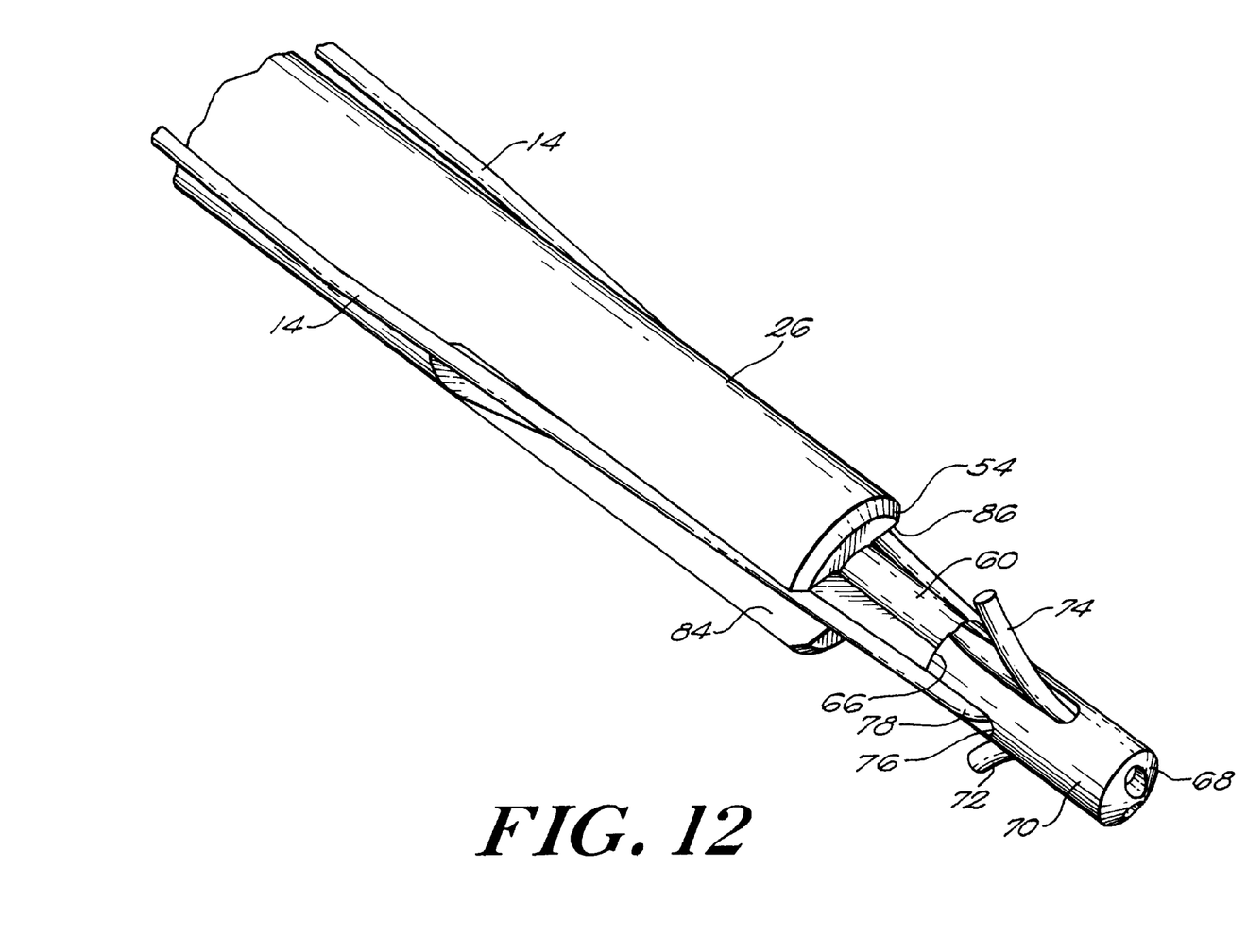
FIG. 12 is a perspective view of the suture anchor inserting member and suture anchor of FIG. 10.

An exemplary suture anchor 12 useful with the system of FIG. 1, and best seen in FIGS. 10 to 12, includes a substantially cylindrical body with a proximal end 66, a distal end 68 forming an apex, a sidewall 70 disposed between the proximal 66 and distal 68 ends and a diameter $D_1$. The suture anchor 12 also has two opposed deformable barbs 72, 74 extending from the sidewall 70. The free ends of the deformable barbs 72, 74 may extend outwardly from the sidewall 70 and proximally (toward the proximal end 66 of the suture anchor 12) such that each barb defines an angle that is between about 10 and 90 with respect to the sidewall 70. More or fewer deformable barbs may be provided as desired to ensure proper retention of the suture anchor 12 within a bone.

The suture anchor 12 further includes a hole 76 that extends in a direction that is transverse to a longitudinal axis of anchor 12. The hole 76 is useful to seat and retain an intermediate portion of suture thread 14 during use of the suture anchor insertion tool 10. Grooves 78 (one shown) may also be provided on opposite sides of the suture anchor 12. These grooves 78 communicate with the hole 76 and extend proximally therefrom.

Generally, the suture anchor 12 may have a diameter $D_1$ between about 1 to 3 mm and a length between about 3 to 12 mm and preferably a diameter $D_1$ between about 1.8 to 2.8 mm and a length between about 5 to 11 mm. The Mitek® Mini Anchor™, available from Mitek Surgical Products, Inc. of Westwood, Mass., is one example of a suture anchor that may be used with the present invention. One of ordinary skill in the art will appreciate that it is possible to use other suture anchor designs within the scope of the invention. One of ordinary skill in the art will further appreciate that suture thread 14 may be constructed from a variety of suture materials. Exemplary materials include, but are not limited to, braided polyester and polydioxanone (PDS).

The system of the invention may also include one or more suture needles 16 preattached to suture thread 14. Each exemplary suture needle 16 (illustrated in FIG. 1) has a first tissue penetrating end 80 and a second trailing end 82. The size and shape of the needles used with the system of the invention may be selected by a person of ordinary skill in the art depending upon the specific application of the system, and in particular, depending upon whether the system is used in an open or closed (e.g. arthroscopic) surgical procedure. Generally, the needles 16 are at least slightly curved. In one embodiment, a needle holder (not shown) includes a length of tubing suitable to hold the penetrating end 80 of each needle 16 within opposite sides of the tubing.

One of ordinary skill in the art will appreciate that the cavity 28 may store more than one type of needle attached to the suture thread, and may contain more than one suture thread attached to the suture anchor. Inclusion of multiple needles or threads within the cavity allows a surgeon the most flexibility to accommodate the challenges of a given surgical procedure.

The suture anchor insertion system of FIG. 1 may be prepared for use by seating the suture anchor 12 on the suture anchor seating element 58, placing the suture needles 16 within the proximal portion 32 of the internal cavity 28, placing a tension on the suture thread 14 by pulling the thread 15 proximally from the suture anchor 12 across the suture retaining member 42 and closing the suture retaining member 42 so as to retain the suture thread 14 in a state of tension (FIG. 7), placing the remainder of the suture thread 14 in the proximal portion 32 of the internal cavity 28, and placing the cover member 36 in its closed position so as to retain the suture needles 16 and suture thread 14 within the internal cavity 28. The suture anchor insertion system is illustrated in this prepared state in FIG. 8.

The suture anchor insertion system of the invention so prepared may be used as follows. A surgeon, using either an open or a closed surgical technique, prepares a bore in a bone suitable for receiving the suture anchor 12. The surgeon applies the suture anchor insertion system so as to align the suture anchor 12 with the bore formed in the bone and inserts the suture anchor 12 into the bore to a depth determined by the surgeon. This depth may be provided my inserting the anchor projecting member 60 partly or completely into the bone. The surgeon next pulls back on the suture anchor insertion tool 10 to set the barbs 72, 74 on the suture anchor 12 within the bone tissue surrounding the preformed bore in the bone. The cover member 76 is then moved to its intermediate position, the suture retaining member 42 is opened and the suture anchor insertion tool 10 is retracted from the surgical site. Next, the cover member 76 is moved to its open position and the suture needles 16 and thread 14 are removed from the internal cavity 28. The surgeon may then use the suture needles 16 and thread 14 to attach the desired tissue to the bone.

It will be understood that the foregoing is only illustrative of the principles of the invention, and that various modifications can be made by those skilled in the art without departing form the scope and spirit of the invention. All references cited herein are expressly incorporated by reference in their entirety.

What is claimed is:

1. A suture anchor insertion system, comprising:
   a handle member having a proximal end, a distal end, and a side wall disposed between the proximal and distal ends, the side wall defining an internal cavity suitable for storing at least one suture needle and suture thread;
   a cover member disposed on the side wall of the handle member and being movable between at least a first, open position and a second, closed position wherein the cover member encloses the internal cavity in a manner sufficient to retain the at least one suture needle and suture thread within the internal cavity, and wherein movement of the cover member from the second, closed position to the first, open position releases the at least one suture needle and at least a portion of the suture thread from within the internal cavity;
   a suture thread retaining member; and
   an elongate suture anchor inserting member extending from the distal end of the handle member and having a suture anchor seating element at a distal end thereof, the suture seating element being effective to releasably seat a suture anchor.

2. The system of claim 1, further comprising a suture anchor releasably seated on the suture anchor seating element.

3. The system of claim 2, further comprising a suture thread having an intermediate portion attached to the suture anchor and two free trailing ends extending at least the length of the suture anchor inserting member.

4. The system of claim 3, further comprising at least one suture needle attached to one of the free trailing ends of the suture thread.

5. The system of claim 4, wherein the free trailing ends of the suture thread and the at least one suture needle are stored in the internal cavity.

6. The system of claim 1, wherein the suture anchor insertion member has a length greater than about 2 inches.

7. The system of claim 6, wherein the suture anchor inserting member includes opposed suture seating grooves.

8. A suture anchor insertion system, comprising:
   a handle member having a proximal end, a distal end, and a side wall disposed between the proximal and distal ends, the side wall defining an internal cavity suitable for storing at least one suture needle and suture thread;
   a cover member disposed on the side wall of the handle member and being movable between at least a first, open position and a second, closed position wherein the cover member encloses the internal cavity in a manner sufficient to retain the at least one suture needle and suture thread within the internal cavity;
   a suture thread retaining member;
   an elongate suture anchor inserting member extending from the distal end of the handle member and having a suture anchor seating element at a distal end thereof, the suture seating element being effective to releasably seat a suture anchor; and a suture thread having an intermediate portion attached to the suture anchor and two free trailing ends extending at least the length of the suture anchor inserting member, wherein the suture thread disposed between the suture thread retaining member and the suture anchor is retained in a state of tension by the suture thread retaining member.

9. The system of claim 8, wherein the suture thread retaining member is disposed on the handle member and comprises a base element for receiving suture thread and a cap element that is selectively matable with the base element to retain the suture thread in a state of tension.

10. The system of claim 9, wherein the base element and the cap element are substantially circular in shape.

11. The system of claim 9, wherein the suture thread retaining member is disposed within the internal cavity of the handle member.

12. The system of claim 9, wherein the suture thread retaining member is made from a polymeric material.

13. The system of claim 9, wherein the cover member encloses the suture thread retaining member when the cover is in its second, closed position.

14. The system of claim 13, wherein the cover member further has an intermediate position wherein the suture thread retaining member is not enclosed by the cover member and a proximal portion of the cavity is enclosed in a manner sufficient to retain the at least one suture needle and suture thread within the internal cavity.

15. The system of claim 9, wherein the suture seating element comprises a flat, distal facing surface and a seating pin extending distally from the flat, distal-facing surface.

16. The system of claim 15, wherein a proximal end of the suture anchor has a pin receiving cavity that is releasably matable with the seating pin.

17. The system of claim 16, wherein the suture anchor is retained on the suture anchor seating element by means of the seating pin and tension on the suture thread.

18. The system of claim 15, wherein the suture anchor is generally cylindrical and the suture seating element has a diameter that is no greater than the diameter of the suture anchor.

19. The system of claim 18, wherein the diameter of the seating element of the suture anchor insertion member and the diameter of the suture anchor are each less than about 3.0 mm.

20. A suture anchor insertion tool, comprising:

a handle member having a proximal end, a distal end, and a side wall disposed between the proximal and distal ends, the side wall defining an internal cavity suitable for storing at least one suture needle and suture thread;

a cover means for selectively opening and closing the internal cavity, the cover means being disposed on the handle member and movable between a first, open position allowing access to the internal cavity and a second, closed position suitable to enclose and retain the at least one suture needle and suture thread within the internal cavity;

a suture thread capturing element, disposed on the handle member, including a base member having a peripheral rim and a cap member that is movable between a first, open position wherein the cap member is spaced apart from the peripheral rim of the base member and a second, closed position wherein the cap member mates with the base member in proximity to the peripheral rim;

an elongate suture anchor inserting member extending from the distal end of the handle member and having a suture anchor seating element at a distal end thereof, the suture seating element being effective to releasably seat a suture anchor.

21. The suture anchor insertion tool of claim 20, wherein the suture thread capturing element is disposed within the internal cavity.

22. The suture anchor insertion tool of claim 20, wherein the cap member mates with the base member by means of a friction fit.

23. The suture anchor insertion tool of claim 22, wherein the base member is generally cylindrical and the peripheral rim is generally round.

24. The suture anchor insertion tool of claim 20, wherein the internal cavity comprises proximal and distal portions and the suture thread capturing element is located in the distal portion of the internal cavity.

25. The suture anchor insertion tool of claim 24, wherein the cover means further includes an intermediate position wherein the suture thread capturing element is not enclosed and the proximal portion of the internal cavity is enclosed in a manner sufficient to retain at least one suture needle and suture thread with the proximal portion of the internal cavity.

26. A suture anchor insertion tool, comprising:

a handle member having a proximal end, a distal end, and a side wall disposed between the proximal and distal ends, the side wall defining an internal cavity having proximal and distal portions and being suitable for storing at least one suture needle and suture thread;

a retaining means for selectively creating tension on a length of suture thread, the retaining means being disposed within the internal cavity;

a sliding door disposed the side wall of the handle and having a first, open position wherein the internal cavity is uncovered so as to allow access to both the proximal and distal portions of the internal cavity;

a second, closed position wherein the door covers the proximal and distal portions of the internal cavity;

a third, partially open position wherein the door covers the proximal portion of the internal cavity sufficient to retain at least one suture needle and thread within the internal cavity, while exposing the distal portion of the internal cavity; and an elongate suture anchor inserting member extending from the distal end of the handle member and having a suture anchor seating element disposed at a distal end thereof, the suture seating element being effective to releasably seat a suture anchor.

27. The tool of claim 26, wherein the retaining means comprises a base member having a peripheral rim and a suture thread retaining cap having a first, open position wherein the cap is spaced apart from the peripheral rim of the base member and a second, closed position wherein the cap mates with the base member in proximity to the peripheral rim wherein a suture thread disposed on the peripheral rim may be retained in a state of tension by placing the cap in its closed position.

28. The tool of claim 27, wherein the retaining means is located in the distal portion of the internal cavity.

* * * * *